(12) United States Patent
Ballenger

(10) Patent No.: US 8,974,427 B2
(45) Date of Patent: Mar. 10, 2015

(54) TRACHEOSTOMY SUPPORT APPARATUS

(76) Inventor: James Ballenger, Mauldin, SC (US)

( * ) Notice: Subject to any disclaimer, the term of this patent is extended or adjusted under 35 U.S.C. 154(b) by 408 days.

(21) Appl. No.: 12/760,506

(22) Filed: Apr. 14, 2010

(65) Prior Publication Data

US 2010/0262093 A1      Oct. 14, 2010

Related U.S. Application Data

(60) Provisional application No. 61/169,274, filed on Apr. 14, 2009.

(51) Int. Cl.
| *A61F 13/15* | (2006.01) |
| *A61F 13/56* | (2006.01) |
| *A61L 15/00* | (2006.01) |
| *A61L 15/44* | (2006.01) |
| *A61M 16/04* | (2006.01) |
| *A47G 9/10* | (2006.01) |
| *A41B 13/10* | (2006.01) |

(52) U.S. Cl.
CPC ......... *A61M 16/047* (2013.01); *A61M 16/0497* (2013.01); *A47G 9/1072* (2013.01); *A41B 13/106* (2013.01); *A47G 9/1045* (2013.01); *A47G 9/1081* (2013.01); *A47G 9/1054* (2013.01); *A41B 13/103* (2013.01); *A61M 16/0488* (2013.01)
USPC ...................... 604/304; 604/308; 128/207.17

(58) Field of Classification Search
CPC ..... A47G 9/10; A47G 9/1045; A47G 9/1054; A47G 9/1072; A47G 9/1081; A47G 9/109; A47G 9/06; A47G 9/064; A47G 9/068; A41B 13/10; A41B 13/103; A41B 13/106; A61M 16/047; A61M 16/04; A61M 2016/04; A61M 2016/0434; A61M 2016/0443; A61M 2016/0445; A61M 2209/088; A61M 2210/06; A61M 16/0497; A61M 16/0465; A61M 16/0488; A61F 13/15; A61F 13/12; A61F 13/128; A61F 2007/0009; A61F 2007/0011
USPC .................. 604/303, 304, 305, 307, 308; 128/207.14, 207.15, 207.16, 207.17; 2/468, 48, 49.1, 49.2, 49.4; 5/417, 418, 5/419, 420; 190/2; 383/4
See application file for complete search history.

(56) References Cited

U.S. PATENT DOCUMENTS

| 2,389,596 | A | * | 11/1945 | Charnas et al. | ............... 224/623 |
| 3,555,580 | A | * | 1/1971 | Willis | ............... 5/636 |
| 4,548,200 | A | * | 10/1985 | Wapner | ........... 128/207.17 |
| 4,884,299 | A | * | 12/1989 | Rose | ............... 206/390 |
| 4,891,846 | A | * | 1/1990 | Sager et al. | ............... 2/48 |
| 4,951,666 | A | * | 8/1990 | Inman et al. | ............... 607/114 |
| 5,016,303 | A | * | 5/1991 | Tanaka et al. | ............... 5/636 |
| 5,163,914 | A | | 11/1992 | Abel | |
| 5,241,706 | A | * | 9/1993 | Netz | ............... 2/66 |
| 5,244,278 | A | * | 9/1993 | Robitaille | ............... 383/4 |
| 5,247,928 | A | * | 9/1993 | Stilts, Jr. | ............... 607/109 |
| 5,509,141 | A | * | 4/1996 | Saltzman | ............... 2/49.2 |
| 5,749,360 | A | | 5/1998 | Lacey | |

(Continued)

*Primary Examiner* — Adam Marcetich
(74) *Attorney, Agent, or Firm* — Additon, Higgins & Pendleton, P.A.

(57) ABSTRACT

A tracheostomy support apparatus incorporates a folded sheet of fabric into a pocket formed at one end of the folded sheet. The support apparatus includes a cradle on an outer surface for holding tubes, hoses, and medical equipment connected between a tracheostomy and adjacent equipment, such as a ventilator. The support apparatus cushions and supports the hoses and tubes associated with a tracheostomy but also absorbs fluids emanating from the tracheostomy.

18 Claims, 5 Drawing Sheets

(56) References Cited

U.S. PATENT DOCUMENTS

| | | | |
|---|---|---|---|
| 5,785,219 A * | 7/1998 | Kraft | 224/576 |
| 5,918,311 A * | 7/1999 | Lampson et al. | 2/49.2 |
| 5,960,471 A * | 10/1999 | Burton | 2/48 |
| 6,023,798 A * | 2/2000 | Hui | 5/490 |
| 6,186,139 B1 * | 2/2001 | Bezicot et al. | 128/200.24 |
| 6,405,378 B1 * | 6/2002 | Garner | 2/102 |
| 6,499,140 B1 * | 12/2002 | Benjamin et al. | 2/49.2 |
| 6,647,570 B1 * | 11/2003 | Ong | 5/485 |
| 6,751,816 B1 * | 6/2004 | Wechsler | 5/417 |
| 7,472,706 B2 | 1/2009 | Weiss | |
| D653,334 S * | 1/2012 | Thompson et al. | D24/128 |
| 8,186,353 B1 * | 5/2012 | LeJeune | 128/207.29 |
| 2001/0029631 A1 * | 10/2001 | Griffin et al. | 5/655 |
| 2002/0078506 A1 * | 6/2002 | Sloot | 5/644 |
| 2003/0074710 A1 * | 4/2003 | Sanders et al. | 2/49.2 |
| 2003/0135925 A1 * | 7/2003 | Higashi et al. | 5/417 |
| 2004/0098781 A1 * | 5/2004 | Sky | 2/49.2 |
| 2006/0010555 A1 * | 1/2006 | Hayes et al. | 2/69 |
| 2006/0059626 A1 * | 3/2006 | Greenleaf | 5/636 |
| 2007/0163027 A1 * | 7/2007 | Hamilton | 2/171 |
| 2007/0199123 A1 * | 8/2007 | Friedland et al. | 2/49.1 |
| 2009/0036960 A1 * | 2/2009 | Blair | 607/109 |
| 2010/0107294 A1 * | 5/2010 | Gillian | 2/49.5 |

* cited by examiner

TRACHEOSTOMY SUPPORT APPARATUS

CROSS REFERENCE TO RELATED APPLICATIONS

This application claims the benefit of priority to and incorporates entirely by reference herein U.S. Provisional Patent Application Ser. No. 61/169,274 (Ballenger) filed on Apr. 14, 2009.

FIELD OF THE INVENTION

The present invention embraces an absorptive tracheostomy tube support apparatus for positioning between a patient's neck and a tracheostomy tube extending into the patient's trachea.

BACKGROUND OF THE INVENTION

A tracheotomy is a common surgical procedure in which a doctor creates an incision into the trachea, forming an opening known as a tracheostomy. The doctor utilizes the tracheostomy for accessing the trachea and placing a tube into the patient's trachea (or "windpipe") to assist with breathing. This artificial airway, commonly referred to as a tracheostomy tube, allows for air to bypass a portion of the windpipe, which may be damaged or obstructed, and ensure proper breathing through the lungs. The tracheostomy tubes are useful for individuals who are currently or have recently been assisted by a ventilator, who have upper airway obstructions, and those who have chronic physical conditions that make normal breathing too difficult to achieve without assistance.

In standard practice, the tracheostomy tube consists of an outer tube inserted into the trachea, an inner tube (or inner cannula) that fits snugly within the outer tube and is removable for replacement purposes, a flange that fits snugly against the patient's neck, and a terminating portion that protrudes from the tracheostomy. The flange is usually adapted with ties that connect around a patient's neck or onto an associated collar for holding the tracheostomy tube in fixed position. The terminating portion of the tracheostomy tube is adapted for connecting with secondary medical equipment such as a ventilator. Needless to say, the tracheostomy tube fitting is complicated and uncomfortable.

A problem arises for patients with tracheostomy tubes, particularly those with associated ventilators, in that the weight of the ventilator connectors pull on the tube. A patient connected to a ventilator also risks injury or damage to the trachea when the patient moves in one direction or the other. The downward force on the tracheostomy tube and the side to side forces caused by the patient moving around may easily irritate the trachea, leading to bleeding or even infection. At worst, these outside forces on the tracheostomy tube may dislodge the tube from its intended position, requiring immediate medical attention.

The medical community and the patients alike would benefit from an apparatus to make the tracheostomy tube more comfortable, more reliable, and less vulnerable to dislodging and irritation. Attempts in this field are summarized below.

U.S. Pat. No. 7,472,706 (Weiss) describes a tracheostomy tube support that includes a tubular cushion having a through hole. The Weiss patent describes that the tubular cushion is preferably made of "soft, skinned, closed-cell polymeric foam such as 'Microcell.'" The closed-cell polymeric foam used to form the tubular cushion has the property of low moisture absorption. A flexible tie for securing the cushion against the neck passes through the through hole. The flexible tie may be tied around the neck or may use hook and loop fasteners to secure the flexible tie to a tracheostomy collar.

U.S. Pat. No. 5,163,914 (Abel) discloses a respirator hose support pad for tracheostomy patients. The support pad includes a soft and somewhat resilient interior covered by a flexible outer material. The support pad is placed across the chest of a tracheostomy patient and near the tracheostomy tube. A belt, which is attached to the support pad, loosely holds the respirator hose so that the respirator hose can move in response to patient movements. This ease of movement helps to prevent unwanted tension and thus patient discomfort. The support pad serves to slightly elevate the respirator hose. A downward angle in the respirator hose is formed in the portion of the respirator hose opposite the tracheostomy tube. This set-up serves to prevent fluid condensation from entering the tracheostomy tube and the patent's lungs. Instead, fluid condensation drains into a collection vial.

U.S. Pat. No. 5,749,360 (Lacey) describes a tracheostomy mask for delivering gaseous therapeutics to a patient fitted with a tracheostomy tube. The mask includes a coupling ring for connecting the mask to a supply tube. A tubular structure within the mask connects the supply tube to the tracheostomy tube. The stabilizer (i.e., the opening of the tubular structure that receives the tracheostomy tube) has an opening larger than the outside diameter of the tracheostomy tube, which allows the mask to move without placing uncomfortable strain on the tracheostomy tube. Moreover, the mask will pull away from the tracheostomy tube without placing undue stress on the tracheostomy tube after the application of a significant force. The mask includes a number of weep holes that provide drainage for fluids (e.g., mucous, phlegm, and excess condensation). The weep holes are positioned so that gravity acts to drain such fluids and thereby prevent the obstruction of the airway.

The above noted patent publications fail to solve certain notable problems in the art of tracheostomy tube support. Namely, the tube support needs to be absorptive, stabilizing, adaptable for variously sized tubes and hoses, and re-usable if desired. Each of these features is discussed in detail below.

BRIEF SUMMARY OF THE INVENTION

A tracheostomy support apparatus incorporates a folded sheet of fabric into a pocket formed at one end of the folded sheet. The support apparatus includes a cradle on an outer surface for holding tubes, hoses, and medical equipment connected between a tracheostomy and adjacent equipment, such as a ventilator. The support apparatus cushions and supports the hoses and tubes associated with a tracheostomy but also absorbs fluids emanating from the tracheostomy.

BRIEF DESCRIPTION OF THE DRAWINGS

The drawings and photographs attached to this application show the invention in various views and cross sections. Each view supports the detailed description as follows.

DETAILED DESCRIPTION

The invention is a tracheostomy tube support apparatus (10) with added functionality. The tracheostomy support apparatus (10) is made of at least one layer of a soft, resilient support fabric (11). This support fabric (11) may be a cotton-based material or a synthetic blend (e.g., polyester, nylon) and has a surface quality that is comfortable against a patient's skin. In one embodiment, the tracheostomy tube support apparatus (10) is a fleeced material (i.e., a "fuzzy surface"), but a fine terry cloth, or even a smooth-surfaced silky support fabric is within the scope of the invention.

One goal of the tracheostomy tube support apparatus (10) is that of support, as the name implies. The support apparatus (10) lifts up and cradles the ventilator hoses (14A) and/or ventilator tubes (14B) extending from a tracheostomy tube (16) and connected to associated ventilators or other medical equipment (not shown). The ventilator tube and ventilator hoses may be referred to collectively as ventilator connectors (14A, 14B).

Figure 1:
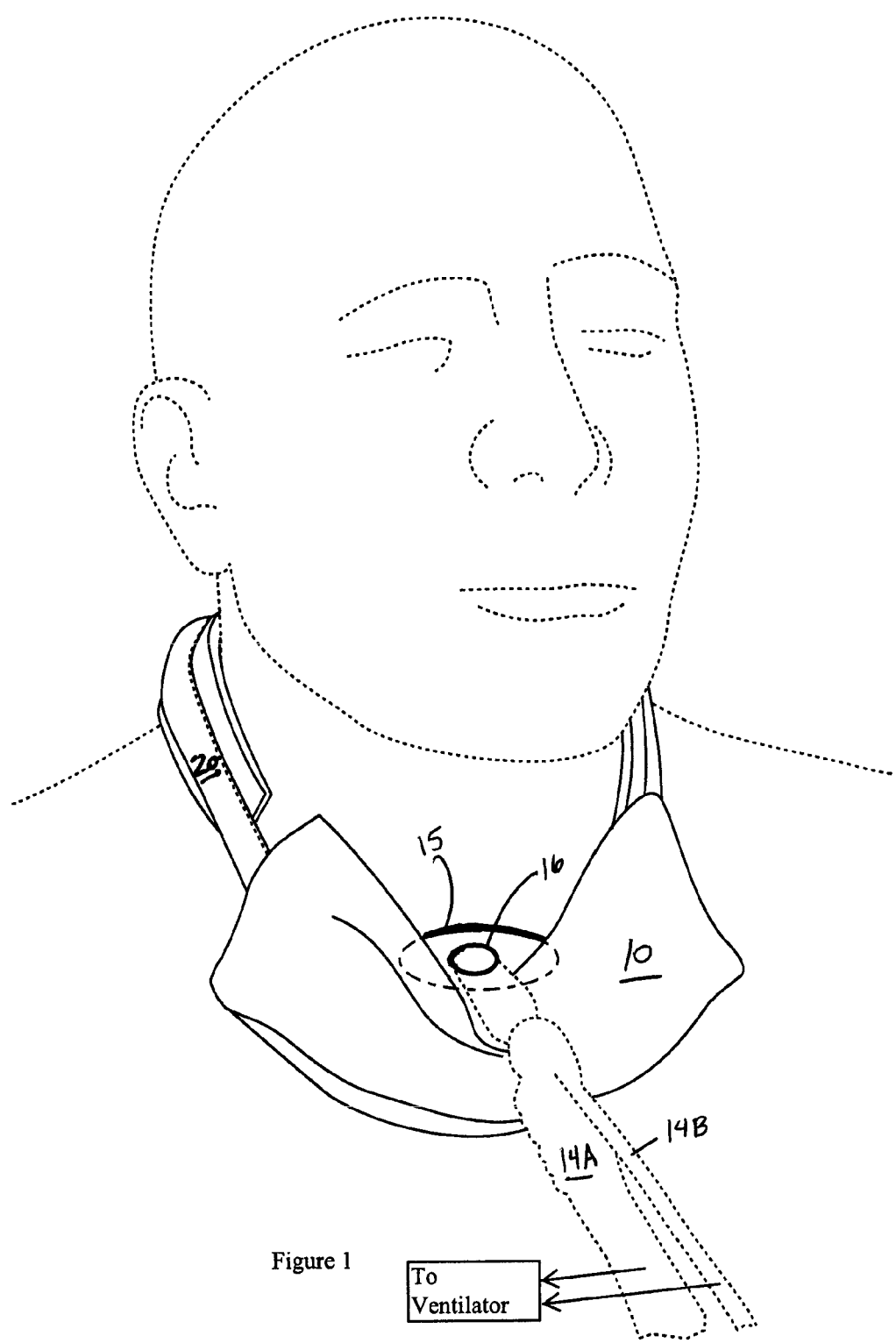
FIG. 1 shows a perspective view of the tracheostomy tube support apparatus of this invention with a neck strap attached.

As shown in FIG. 1, the tracheostomy tube (16) is held in place with a tracheostomy plate (15). The tracheostomy tube (16) and the tracheostomy plate (15) are well known in the art of tracheostomy equipment. The tracheostomy tube (16) is adapted to mate with ventilator connectors to provide air access from the ventilator or other medical equipment. Without limiting the invention in any way, the tracheostomy tube support apparatus (10) lifts and supports the ventilator hoses and tubes (14A, 14B) so that they maintain a better connection to the tracheostomy tube (16) jutting out from the patient's neck.

The support apparatus (10) can be placed in a variety of positions between the ventilator and the tracheostomy tube (16). FIG. 1 shows the support apparatus lifting the ventilator hose and ventilator tube (14A, 14B) to maintain proper alignment with the tracheostomy tube. By moving the support apparatus (10) closer to the patient's tracheostomy incision, the support apparatus can also support the tracheostomy tube (16) if the patient finds that more comfortable. Of course, the patient may prefer that the support apparatus (10) be positioned farther down the patient's chest to support the ventilator connections (14A, 14B) at a lower point on the patient's body closer to the abdomen.

To accomplish this supporting function, the tracheostomy tube support apparatus (10) has a thickness sufficient to lift the ventilator connections (14A, 14B) off a patient's body when the tracheostomy tube support apparatus (10) is positioned between the patient's body and the tracheostomy tube (16). By maintaining a consistent elevation between the tracheostomy tube (16) and any outside hoses and tubes (14A, 14B) to a ventilator, the tracheostomy tube support apparatus (10) makes the surgically implanted tracheostomy tube more stable. This is helpful to the patient because patient movement causes the ventilator connectors (14A, 14B) to shift, which, in turn, shifts the tracheostomy tube (16). Shifting the tracheostomy tube (16) can cause skin abrasions, bleeding, and incision irritations that are more likely to become infected. In this regard, the support apparatus (10) holds the ventilator connections to avoid the shifting that leads to other problems.

Figure 5:
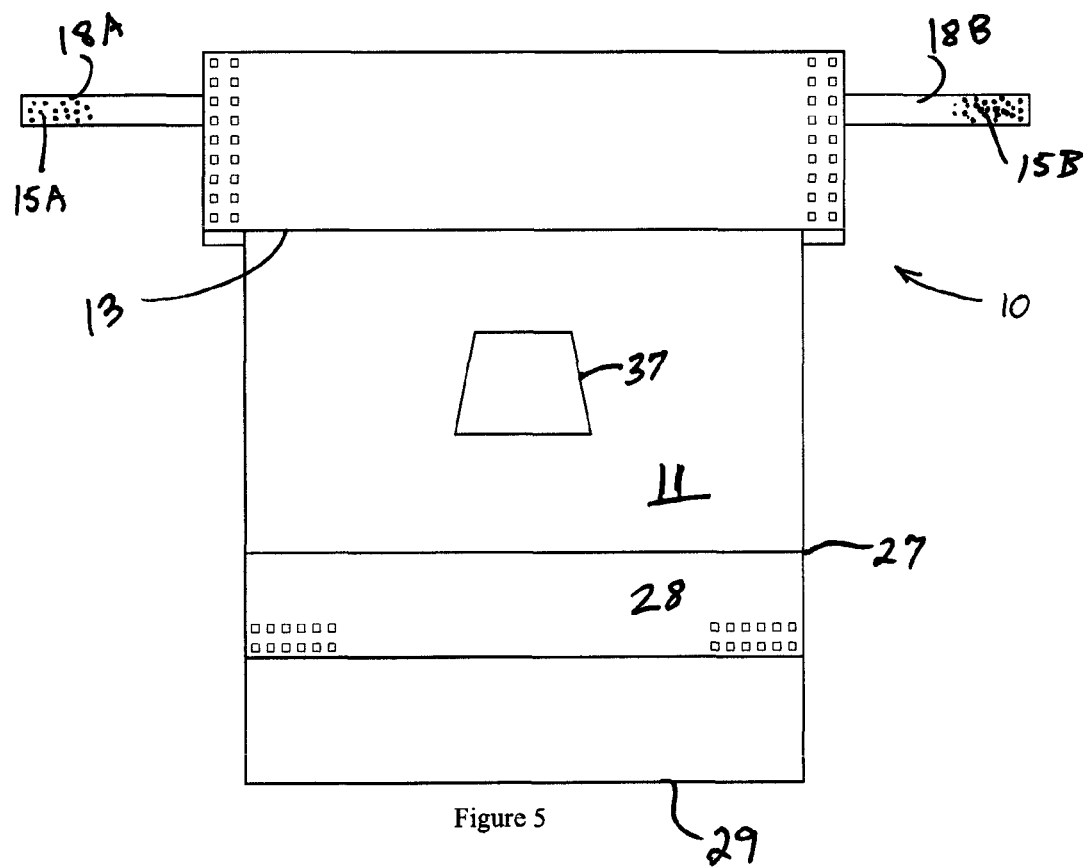
FIG. 5 is a schematic diagram showing the tracheostomy support apparatus after the folding operation of FIG. 3.

The tracheostomy tube support apparatus (10) has a sufficient thickness to achieve its supporting and stabilizing function. This thickness may be formed of a single sheet of support fabric (11) that rolls up to form folded layers (25) of the soft and resilient material. To avoid the problem of having to re-roll the fabric or inconsistent results in rolling the fabric to a desired thickness, the invention encompasses a structure that utilizes a single sheet of support fabric (11) having at least one side with a soft, fleecy surface. A hem (27) on one end of the sheet of support fabric (11) may provide a template for the size of the folds (25). In the representation of FIG. 5, the fabric is hemmed so that the user may fold the fabric to approximately twice the width of the hemmed portion (28), thereby shortening the length of a single sheet of support fabric (11) at the fold (29).

The other end of the sheet forms a pocket (13) in which the folded sheet of support fabric (11) fits for a snug and reliably uniform shape. The sheet of support fabric (11) is conditioned for rolling in a way such that the softer side is positioned adjacent the patient's skin. After rolling up the fabric into folded layers (25), in a size that is roughly proportional to the hemmed portion (28), and fitting the roll into the associated pocket (13), the tracheostomy tube support apparatus (10) is ready for positioning on the patient with the open side of the pocket (13) (shown in FIG. 2B) facing away from the patient's skin. The smoother side of the apparatus (30), opposite the pocket (13) is on the patient's skin. See FIG. 5.

The soft nature of the fabric allows the tracheostomy tube and associated equipment to be cradled within the support apparatus (10). The tracheostomy tube support apparatus (10) fits any size of tubes and will hold the tubes by allowing hoses and tubes, such as those associated with ventilators, to sink flexibly into the tracheostomy tube support apparatus (10). This feature holds the variously sized tubes in a stable, cradled position on and in the support fabric of the support apparatus (10). In other words, the tracheostomy tube and associated equipment are not merely resting on the surface of the support apparatus (10) but are held within it due to their own weight sinking into the fabric. In this way, the tracheostomy tube support apparatus (10) moderates the movement of the tube in every plane.

Figure 2A:
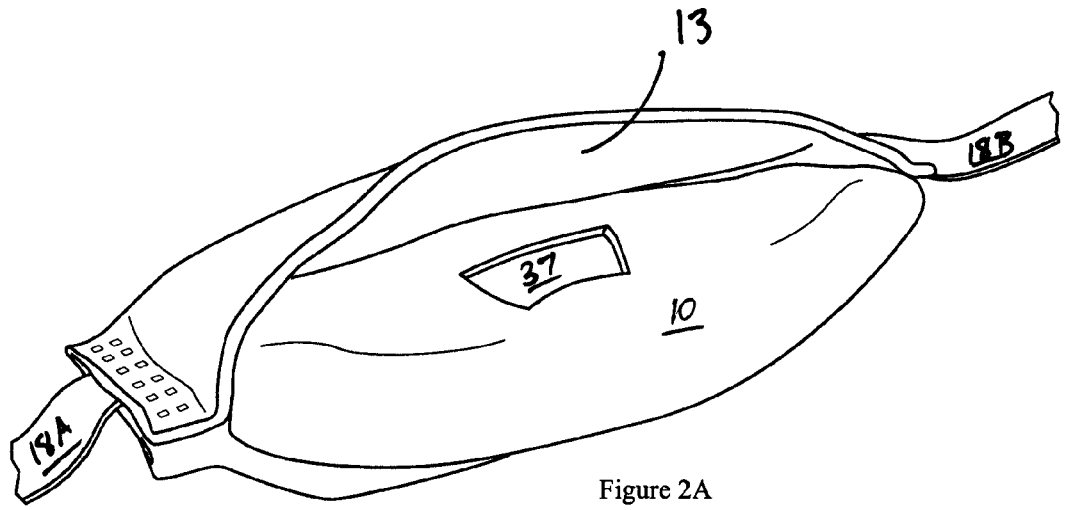
FIG. 2A shows the tracheostomy tube support apparatus according to FIG. 1 with an interior cut-out exposed and with side straps on either end.
Figure 2B:
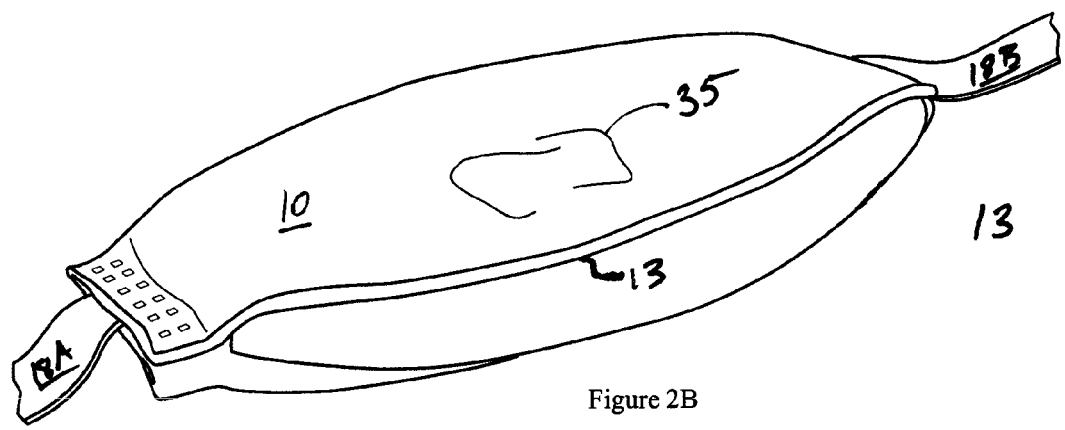
FIG. 2B shows the tracheostomy tube support apparatus according to FIG. 1 with an interior cut-out forming an indentation on the outer surface.
Figure 3:
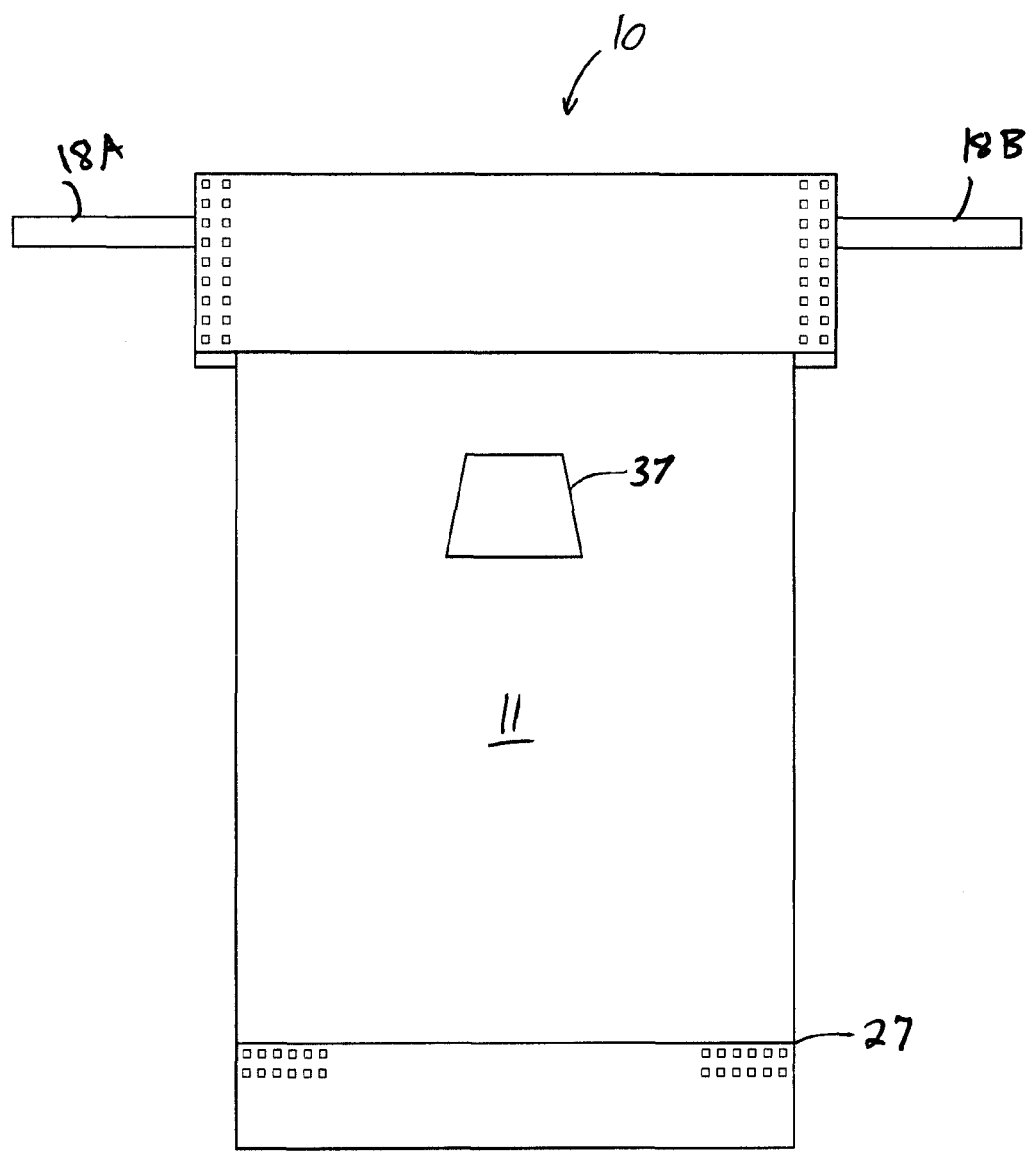
FIG. 3 shows the tracheostomy tube support apparatus with the support fabric unfolded and extending from an opening in the tracheostomy tube support apparatus.
Figure 4:
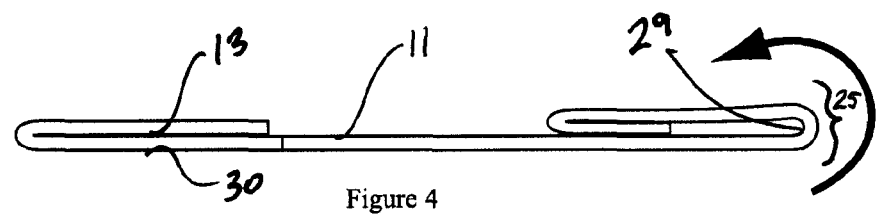
FIG. 4 is a schematic diagram showing the folding of one end of the support fabric of FIG. 3.
Figure 6:
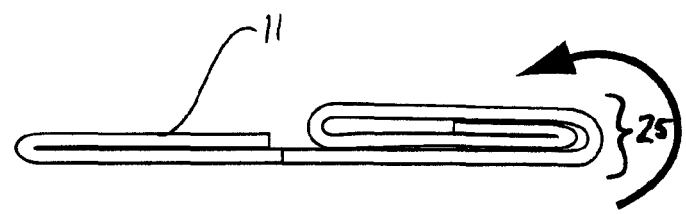
FIG. 6 is a schematic diagram showing another folding process of the support fabric of FIG. 3.
Figure 7:
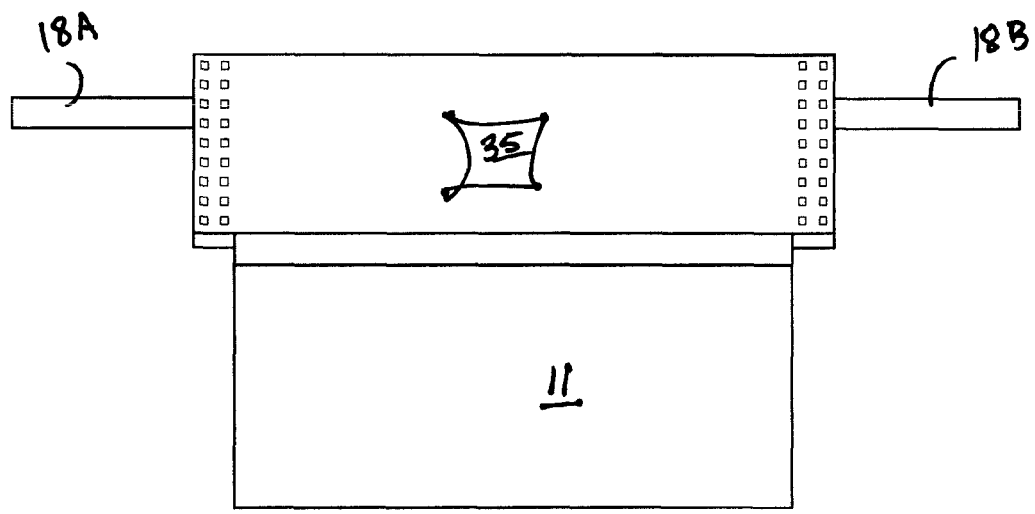
FIG. 7 is a top plan view the tracheostomy tube support apparatus subject to the folding process of FIG. 6.

In one embodiment, the support apparatus (10) is engineered to engage tubes and hoses extending between the tracheostomy and ventilator connectors (15). The tracheostomy support apparatus (10) includes a cradle (35) on its outer surface. This cradle (35) is shaped as an indention or other concave surface slope to hold ventilator connections (14A, 14B), tracheostomy tube (16), and/or other medical equipment connected to the tracheostomy tube therein. As shown in FIGS. 3 and 5, this cradle (35) may be enhanced by forming a cut-out (37) in the sheet of support fabric (11). In this regard, the sheet of support fabric (11) defines the boundaries of a cut-out (37), or void, in the sheet of support fabric (11). As shown in FIG. 2A, the perimeter of the cut-out (37) may be positioned within the interior of the support fabric (11) so that when the support fabric (11) is folded, as in FIGS. 4 and 6, the cut-out helps form the indentation (35). The ventilator connectors (14A, 14B) rest in the cradle to a deeper level within the folded support fabric (11) because of the void therein.

In a different embodiment, the cradle (35) may be formed by embroidering parts of the support fabric (11). The cradle (35) may also be woven into the fabric itself. In this regard, the cradle (35) may be formed when the fabric is formed or formed afterwards. With these embodiments, the cut-out may not be necessary, as sewing the fabric may suffice to form a cradle of sufficient depth to hold the ventilator connectors. Overall, whether the support fabric (11) includes a cut-out, embroidery, sewing, or contoured weaves, the support apparatus (10) holds the ventilator connectors (14A, 14B) and/or the tracheostomy tube (16) in a cradle (35) formed on the surface of the support apparatus (10).

As noted above, another favorable criterion for the support fabric (11) used in forming the support apparatus (10) is that of absorptiveness. The support fabric (11) is permeable to body fluids, water, and the like and retains the fluids. In one embodiment, the support fabric may have wicking properties that move the fluid into the support apparatus and away from the patient's skin. Wicking fibers in the support apparatus move fluid toward the center of the support apparatus. The number of folds of the fabric and the thickness of the fabric may be engineered with absorption in mind. An absorptive fabric is useful for catching fluid emission from a tracheostomy. For example, a recently formed tracheostomy will bleed due to the nature and depth of the incision. An absorptive support apparatus (10) aids in removing that blood from the patient's wound and ensuring a more hygienic area around the tracheostomy. In other embodiments, the tracheostomy tube support apparatus (10) may be useful in applying medications to the wounds. Even tracheostomy tubes that have been in place for some time may tend to leak fluids, especially mucus or even fluids associated with infection. The support fabric (11) used in the invention described herein is sufficiently absorptive to catch these fluids and halt the discomfort and germ progression associated with such weeping from the tracheostomy.

In one embodiment, the support apparatus (10) incorporates hygienic additives such as, but not limited to, antimicrobial, anti-bacterial, and/or anti-fungal coatings or particles in the support apparatus. These hygienic additives may be incorporated into the fiber of the support fabric (11) (i.e., the fabric is made of strands that include the hygienic materials) during the fabric manufacturing process, or the hygienic materials may be topically applied after the device has been made. These hygienic additives allow for longer use of the support apparatus and make it more appropriate for use near the incision of a tracheostomy.

Another useful feature of the tracheostomy tube support apparatus is its ability to be used with current tracheostomy tube support collars and existing flanges and plates on a tracheostomy tube. The support apparatus (10) includes respective end straps (18A, 18B) with hook and loop attachment mechanisms (15A, 15B) for connecting the support apparatus (10) to the patient's currently existing tracheostomy plate, or collar (15). In those embodiments that do not require a separate collar or plate (15), the tracheostomy tube support apparatus (10) includes a separate neck strap (20) that is attachable to the end straps (18) for fitting around the patient's neck and holding the support apparatus in place. The neck strap (20) is entirely removable via standard attachment mechanisms (15). Overall, the end straps, neck straps, and stitching in the support apparatus are made of materials and combinations of materials that are soft and non-irritating to the patient's skin. In other words, the exposed finishes on these parts of the apparatus are silky, slick, and smooth.

After use or between uses, the tracheostomy tube support apparatus (10) can be unrolled and thoroughly washed. By using a folded construction, the tracheostomy tube support apparatus (10) is amenable to soaking and washing in a way that a cylindrical-only or tubular shape is not. The tracheostomy tube support apparatus of this invention is, therefore, re-usable as desired. The drawings showing the rolling and unrolling of the support fabric are not limiting, as the support apparatus (10) may be sewn together along its sides in the folded position so that the device cannot be unrolled after manufacture.

In the drawings and the specification, typical embodiments of the invention have been disclosed. Specific terms have been used only in a generic and descriptive sense, and not for purposes of limitation. Unless otherwise noted, the inventor is not acting as a lexicographer, and terms herein are intended to have their ordinary meaning. The invention is not restricted to the slavish imitation of each and every detail set forth above. Obviously, devices may be provided which change, eliminate, or add certain specific details without departing from the scope of the invention. The scope of the invention is set forth in the following claims.

The invention claimed is:

1. A tracheostomy tube support apparatus comprising:
a single sheet of fabric that absorbs bodily fluid emitted from a tracheostomy, said single sheet defining a plurality of folded layers such that one end of said single sheet is surrounded by the folded layers, said single sheet further defining a pocket at an other end of said single sheet,
wherein an entirety of said folded layers fits within the pocket; and
wherein said single sheet of fabric defines a cut-out entirely surrounded by the fabric forming an outermost folded layer,
wherein said pocket comprises a top panel folded over a bottom panel; and
said outermost folded layer positioned into the pocket such that the top panel of said pocket is directly adjacent the entire cut-out in the outermost folded layer within the pocket to define a cradle on said top panel of the pocket.

2. A tracheostomy tube support apparatus according to claim 1, wherein the fabric is formed into a sufficient thickness to cradle a tube of varying diameters connected to a tracheostomy.

3. A tracheostomy tube support apparatus according to claim 1, wherein the fabric is fleece.

4. A tracheostomy tube support apparatus according to claim 1, wherein the apparatus moderates movement of a tracheostomy tube in every plane.

5. A tracheostomy tube support apparatus according to claim 1, further comprising a neck strap that is removable from said single sheet of fabric.

6. A tracheostomy tube support apparatus according to claim 1, further comprising end straps.

7. A tracheostomy tube support apparatus according to claim 6, further comprising an attachment mechanism on each end strap for connecting the support apparatus to peripheral equipment or to a neck strap.

8. A tracheostomy tube support apparatus according to claim 1, wherein the apparatus has a thickness of 2 inches or less.

9. A tracheostomy tube support apparatus according to claim 1, wherein said cradle comprises a shape sewn into said support apparatus.

10. A tracheostomy tube support apparatus according to claim 1, further comprising hygienic additives.

11. A tracheostomy tube support apparatus according to claim 10, wherein said hygienic additives are selected from the group consisting of antifungal additives, anti-bacterial additives, anti-dust mite additives, anti-microbial additives, and combinations thereof.

12. A tracheostomy support apparatus comprising:
a single sheet of fabric defining a pocket at a first end and a remaining portion between the pocket and a second end of said single sheet, wherein said remaining portion defines a plurality of folded layers that fit entirely within the pocket,
wherein said pocket comprises a top panel folded over a bottom panel; and
a neck strap that is selectively connected to and removable from said single sheet of fabric;
wherein said single sheet of fabric defines a cut-out entirely surrounded by the fabric forming an outermost folded layer, said outermost folded layer positioned into the pocket such that the top panel of said pocket is directly adjacent the entire cut-out in the outermost folded layer within the pocket to define a cradle on said top panel of the pocket.

13. A tracheostomy support apparatus according to claim 12, wherein said single sheet is absorptive.

14. A tracheostomy support apparatus according to claim 12, wherein the apparatus is placed on a patient's body between a ventilator and a tracheostomy tube installed in the patient's body.

15. A combination of a tracheostomy support apparatus and a tracheostomy tube comprising:
a single sheet of fabric that absorbs body fluids, said single sheet defining a pocket at a first end and a remaining portion between the pocket and a second end of said single sheet,
wherein said remaining portion of said single sheet defines a cut-out, and
wherein said remaining portion is folded into folded layers that fit within the pocket such that the cut-out is directly adjacent and covered by a surface of the pocket; and
a cradle in the exterior surface of the pocket defined by the cutout; and
a tracheostomy tube positioned in the cutout.

16. A tracheostomy support apparatus according to claim 15, wherein the apparatus is placed on a patient's body between a ventilator and said tracheostomy tube installed in the patient's body to support a ventilator hose.

17. A tracheostomy support apparatus according to claim 15, further comprising a removable neck strap.

18. A tracheostomy support apparatus according to claim 15, further comprising end straps.

\* \* \* \* \*